United States Patent
Kaneko et al.

(10) Patent No.: US 8,709,450 B2
(45) Date of Patent: Apr. 29, 2014

(54) CELLULOSE DERIVATIVE AND HYDROGEL THEREOF

(75) Inventors: Hiroaki Kaneko, Hino (JP); Nobuyuki Endo, Hino (JP); Masaya Ito, Hino (JP)

(73) Assignee: Teijin Limited, Osaka (JP)

( * ) Notice: Subject to any disclaimer, the term of this patent is extended or adjusted under 35 U.S.C. 154(b) by 384 days.

(21) Appl. No.: 12/808,613

(22) PCT Filed: Dec. 17, 2008

(86) PCT No.: PCT/JP2008/073500
§ 371 (c)(1),
(2), (4) Date: Jun. 16, 2010

(87) PCT Pub. No.: WO2009/078492
PCT Pub. Date: Jun. 25, 2009

(65) Prior Publication Data
US 2011/0129505 A1 Jun. 2, 2011

(30) Foreign Application Priority Data

Dec. 17, 2007 (JP) ................................. 2007-324570
Feb. 28, 2008 (JP) ................................. 2008-047753

(51) Int. Cl.
*C08B 11/193* (2006.01)
*C08B 1/00* (2006.01)
*C08B 11/15* (2006.01)
*C08B 11/12* (2006.01)
*A61K 9/00* (2006.01)

(52) U.S. Cl.
USPC ................ 424/400; 536/56; 536/90; 536/93; 536/98

(58) Field of Classification Search
USPC .................. 424/488, 400; 536/56, 90, 93, 98
See application file for complete search history.

(56) References Cited

U.S. PATENT DOCUMENTS

| 4,708,821 A | 11/1987 | Shimokawa et al. | |
|---|---|---|---|
| 2005/0187137 A1* | 8/2005 | Pegelow et al. ............... | 510/510 |

FOREIGN PATENT DOCUMENTS

| CN | 1370539 A | 9/2002 |
|---|---|---|
| EP | 1 659 143 A1 | 5/2006 |
| EP | 1 911 769 A1 | 4/2008 |
| EP | 2 311 883 A1 | 4/2011 |
| JP | 62-112604 A | 5/1987 |
| JP | 2000-51343 A | 2/2000 |
| JP | 2004-51531 A | 2/2004 |
| JP | 2007/002063 A | 1/2007 |
| WO | 89/10940 A1 | 11/1989 |
| WO | 92/20349 A1 | 11/1992 |
| WO | 01/46265 A1 | 6/2001 |

OTHER PUBLICATIONS

International Search Report for PCT/JP2008/073500 dated Apr. 14, 2009.
Extended European Search Report for Application No. 08860912.8 dated Mar. 19, 2013.

* cited by examiner

*Primary Examiner* — Ernst Arnold
*Assistant Examiner* — Jianfeng Song
(74) *Attorney, Agent, or Firm* — Sughrue Mion, PLLC

(57) ABSTRACT

The invention is a cellulose derivative wherein some of the carboxyl groups of the cellulose derivative carboxymethylcellulose are replaced with —CO—NH—X—CO—Y—Z, and a hydrogel of the same. In the formula, X is a C1-10 divalent hydrocarbon group, Y is a divalent group derived from polyalkylene oxide having oxygen atoms at both ends, and Z is a C1-24 hydrocarbon group or —CO—$R^4$, where $R^4$ is a C1-23 hydrocarbon group. The hydrogel has excellent viscoelasticity and can be injected into prescribed sites with injecting devices such as syringes, and it can thus be utilized as a medical gel or adhesion barrier.

16 Claims, No Drawings

CELLULOSE DERIVATIVE AND HYDROGEL THEREOF

CROSS REFERENCE TO RELATED APPLICATIONS

This is a National Stage of PCT/JP2008/073500 filed Dec. 17, 2008, which claims priority from Japanese Patent Application No. 2007-324570 filed Dec. 17, 2007, and Japanese Patent Application No. 2008-047753 filed Feb. 28, 2008.

TECHNICAL FIELD

The present invention relates to a cellulose derivative obtained by replacing the carboxyl groups of the cellulose derivative carboxymethylcellulose with a specific substituent, and to a hydrogel thereof. The cellulose derivative of the invention forms a hydrogel in water. The hydrogel has excellent viscoelasticity and can form an amorphous injectable gel that can be injected into prescribed sites with injecting devices such as syringes, and it can therefore be suitably utilized as a medical gel or adhesion barrier.

BACKGROUND ART

Carboxymethylcellulose, derived from the naturally-derived biomass cellulose, is a water-soluble derivative with good dispersibility and water retention, and it is therefore used in a variety of fields including foods and cosmetics. The high safety of carboxymethylcellulose allows it to be utilized in medical fields as a raw material for pap materials, X-ray contrast agents, tablet disintegrating materials, medicinal syrups and adhesion barriers.

Insoluble derivatives formed by modification of the carboxyl groups of carboxymethylcellulose are known, and an example thereof is disclosed in International Patent Publication No. WO01/046265, which describes a polyanionic polysaccharide water-insoluble derivative obtained by combining a carboxymethylcellulose-containing polyanionic polysaccharide, a nucleophilic reagent and an activating reagent in an aqueous mixture, as well as a method for producing it.

The derivative described therein is water-insoluble, and therefore the publication does not describe a gel according to the invention, which is a gel exhibiting a water-soluble property when present in a low concentration in water, but at high concentration exhibiting viscoelasticity such that it does not flow even when inclined.

International Patent Publication No. WO89/10940 describes total and partial esters of acidic polysaccharides selected from the group consisting of carboxymethylcellulose, carboxymethyl starch and carboxymethylchitin, with aliphatic, aryl aliphatic, alicyclic and heterocyclic alcohols, and salts of those partial esters with inorganic or organic bases. However, it makes no reference to formation of hydrogels by these polysaccharide derivatives, nor does it suggest providing an injectable gel according to the invention.

Japanese Patent Application Publication No. 2000-51343 discloses a natural wound-healing product comprising a polysaccharide polymer and one fatty acid chain attached to the polysaccharide polymer, which undergoes a reversible change of state from a gel to a liquid state and back.

However, the polysaccharides disclosed in these publications have poor viscoelasticity in aqueous solution, and therefore cannot be easily applied as hydrogels that are injectable into the body through narrow tubes such as injection needles.

DISCLOSURE OF THE INVENTION

It is an object of the invention to provide a biodegradable cellulose derivative that is useful as an injectable gel which has high viscoelasticity but can also be injected at prescribed sites with injecting devices such as syringes. With hitherto disclosed technology it has not been possible to obtain highly viscoelastic gels because attempts to increase the proportion of introduced substituents (degree of substitution) to obtain high viscoelasticity gels has resulted in agglutination or precipitation. However, a highly viscoelastic gel can remain for any fixed period at a desired site in the body and is therefore useful for protecting wounds and forming physical isolation barriers between organs. In addition, it is possible to produce a local drug delivery system by impregnating a drug into such a gel. Moreover, the property of decomposing or being absorbed upon injection into the body renders it suitable for use as an injection gel material or a scaffolding material for regenerative medicine.

As a result of much diligent research with the aim of discovering an injectable gel with excellent safety and excellent handling that can be used in vivo, the present inventors have found that an injectable gel with high viscoelasticity and excellent handling can be obtained by chemical modification of carboxymethylcellulose with specific functional groups, and the invention has been completed upon this finding.

Specifically, the invention is a cellulose derivative comprising the chemical structure represented by the following formula (1) as a repeating unit.

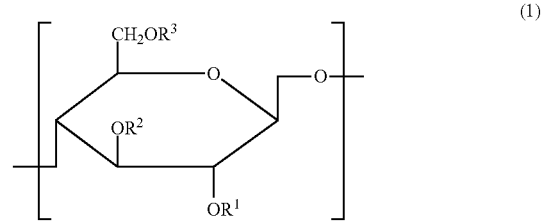

(1)

In formula (1), $R^1$, $R^2$ and $R^3$ are each independently selected from the group consisting of the following formulas (a), (b) and (c):

—H     (a)

—CH$_2$—COOM     (b)

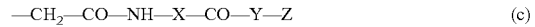

—CH$_2$—CO—NH—X—CO—Y—Z     (c)

where in formula (b), M is hydrogen, an alkali metal or an alkaline earth metal, and in formula (c), X is a C1-10 divalent hydrocarbon group, Y is a divalent polyalkylene oxide with oxygen atoms at both ends and Z is a C1-24 hydrocarbon group or —CO—$R^4$ (where $R^4$ is a C1-23 hydrocarbon group).

The invention further provides a hydrogel comprising the cellulose derivative.

The invention still further provides a medical material comprising the cellulose derivative.

The invention still further provides an adhesion barrier comprising the cellulose derivative.

The cellulose derivative of the invention has the chemical structure represented by formula (1) above as a repeating unit, but it is not limited to a polymer having exactly the same repeating units linked together, and the invention also encompasses polymers having different repeating units linked together based on different combinations of $R^1$, $R^2$ and $R^3$ groups, within the allowable range described above.

BEST MODE FOR CARRYING OUT THE INVENTION

The invention is a cellulose derivative comprising the chemical structure represented by formula (1) above as a repeating unit.

M is hydrogen, an alkali metal or an alkaline earth metal, and sodium, potassium and lithium may be mentioned as alkali metals while magnesium and calcium may be mentioned as alkaline earth metals. Sodium is preferred, however.

X in formula (c) is a C1-10 divalent hydrocarbon group. Specifically, there may be mentioned methylene, ethylene, n-propylene, isopropylene, n-butylene and isobutylene. Methylene is preferred, however.

Y is a divalent group derived from a polyalkylene oxide, having oxygen atoms at both ends. Specifically, a polyalkylene oxide is a polyalkylene ether such as polyethylene glycol, polypropylene glycol or polybutylene glycol. A group having oxygen atoms at both ends is a structure of polyalkylene oxide having the hydrogens removed from the hydroxyl groups at both ends, that contributes to bonding with adjacent groups. Specifically, there may be mentioned groups derived from 1,2-polypropyleneglycols represented by —(O—CH$_2$—CH(CH$_3$)—)$_n$—O—, 1,3-polypropyleneglycols represented by —(O—CH$_2$—CH$_2$—CH$_2$—)$_n$—O— and polyethylene glycols represented by —(O—CH$_2$—CH$_2$—)$_n$—O—. It may also be a group derived from a copolymer of polyethylene glycol and polypropylene glycol, such as a copolymer represented by PEO-PPO, for example. Here, n represents the number of repeating units.

The number of repeating units n is preferably 2-100 and more preferably 3-70.

Z is a C1-24 hydrocarbon group or —CO—R$^4$, and R$^4$ is a C1-23 hydrocarbon group.

Specific examples of C1-24 hydrocarbon groups for Z include straight-chain alkyl groups such as methyl, ethyl, propyl, butyl, pentyl, hexyl, octyl, nonyl, lauryl and stearyl, alkyl groups with cyclic structures such as cyclohexyl, cyclopentyl, cyclohexylnonyl and cholesteryl, unsaturated alkyl groups such as oleyl, and aromatic hydrocarbon groups such as phenyl, naphthyl and benzyl. Stearyl and oleyl groups are preferred among these.

R$^4$ is a C1-23 hydrocarbon group. Specific examples for R$^4$ include straight-chain alkyl groups such as methyl, ethyl, propyl, butyl, pentyl, hexyl, octyl, nonyl, heptadecanyl, heptadecenyl, lauryl and stearyl, alkyl groups with cyclic structures such as cyclohexyl, cyclopentyl, cyclohexylnonyl and cholesteryl, unsaturated alkyl groups such as oleyl, and aromatic hydrocarbon groups such as phenyl, naphthyl and benzyl. Heptadecanyl and heptadecenyl groups are preferred among these.

When R$^4$ is an aliphatic alkyl group, —CO—R$^4$ in Z will be an acyl group derived from a fatty acid. As preferred examples of such acyl groups there may be mentioned lauroyl, palmitoyl, stearoyl and oleoyl. When R$^4$ is an aromatic group, on the other hand, —CO—R$^4$ in Z will be an acyl group derived from an aromatic fatty acid. Preferred examples thereof include benzoyl and naphthoyl. Stearoyl and oleoyl groups are preferred among these.

The degree of substitution is the equivalent of each substituent, where 3 is the total equivalents of substituent (a), substituent (b) and substituent (c). The total of the degree of substitution of substituent (b) and the degree of substitution of substituent (c) is preferably 0.3-2.0, more preferably 0.5-1.8 and even more preferably 0.6-1.2.

The proportion of the degree of substitution of substituent (b) and the degree of substitution of substituent (c) is not particularly restricted, but preferably substituent (b) is present in a greater amount than substituent (c). Particularly preferred as a gel is a structure wherein Rc/b, as the ratio of the degree of substitution of substituent (c) to the degree of substitution of substituent (b), is 0.01-0.4.

The degree of substitution of substituent (c) is 0.001-0.50 and preferably 0.005-0.40. By limiting the degree of substitution of substituent (c) to within this range, it is possible to obtain a gel with suitable viscoelasticity, that is injectable using a narrow tubular instrument such as a syringe. The degree of substitution of substituent (c) can be determined from the ratio of the carbon content and the nitrogen content by elemental analysis.

The weight-average molecular weight of the cellulose derivative is $1 \times 10^3$ to $5 \times 10^6$, preferably $5 \times 10^4$ to $5 \times 10^6$ and more preferably $5 \times 10^4$ to $1 \times 10^6$. The weight-average molecular weight of the cellulose derivative will increase above that of the cellulose derivative before introduction of substituent (c), due to the change in molecular weight by introduction of substituent (c) into the cellulose. By appropriately selecting the molecular weight of the carboxymethylcellulose used as the raw material it is possible to obtain a cellulose derivative with the desired molecular weight.

The carboxymethylcellulose used as the raw material is derived from cellulose. The cellulose may be plant-derived cellulose or bacterial cellulose produced by fermentation, without any particular restrictions. The carboxymethylcellulose can be obtained by converting the cellulose to alkaline cellulose with a strong aqueous alkali solution such as sodium hydroxide, and then reacting this with monochloroacetic acid or its sodium salt. The location of substitution of the carboxymethyl group on the cellulose backbone is not particularly restricted, but preferably it is mainly at the C6 position.

The cellulose derivative of the invention can be obtained by condensation reaction between (i) carboxymethylcellulose and (ii) component P represented by the following formula (2).

Component P is a compound with an amino group at one end, and it is represented by the following formula (2).

H$_2$N—X—CO—Y—Z                        (2)

The definitions of X, Y and Z are the same as for formula (1) above. The amino group is not particularly restricted and it may be one forming a salt with a suitable acid, or a free amino group. The compound of formula (2) is preferably produced by the following reaction.

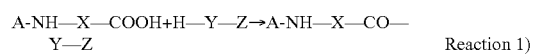

A-NH—X—COOH+H—Y—Z→A-NH—X—CO—Y—Z        Reaction 1)

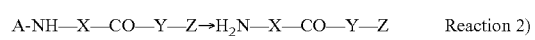

A-NH—X—CO—Y—Z→H$_2$N—X—CO—Y—Z        Reaction 2)

Here, A represents an amino protecting group.

Reaction 1) is a coupling reaction between an amino group-protected amino acid derivative represented by A-NH—X—COO—, and a compound having the structure H—Y—Z and a hydroxyl group on one end. A condensation agent that forms an ester bond is preferably used in the reaction, and a condensation agent such as a carbodiimide is preferably used.

Dicyclohexylcarbodiimide may be mentioned as a specific preferred example.

The amino protecting group A may be a known protecting group such as, specifically, a benzyl group or t-butyloxycarbonyl group (Boc group). A Boc group is preferred among these.

The A—NH—X—CO—Y—Z compound obtained by reaction 1) is not limited to one obtained by the coupling reaction (reaction 1) described above, and any known synthesis process may be employed. For example, it may be synthesized by transesterification reaction between an amino-protected amino acid derivative with the carboxyl group as an active ester, and a compound having the structure H—Y—Z and a hydroxyl group on one end.

Reaction 2) is an amino group deprotecting reaction, and any reaction method may be employed so long as it is a known reaction commonly used for peptide synthesis. When A is a Boc group, deprotecting reaction using an acid is preferred, with trifluoroacetic acid as the preferred acid. There are no particular restrictions on the method of purifying the reaction product, and separation and purification may be carried out by chromatography as desired.

Reactions 1) and 2) may be liquid phase synthesis or solid phase synthesis, and there are no particular restrictions on the reaction methods or purification methods.

A cellulose derivative of the invention can be obtained by coupling reaction between the amino group at one end of $H_2N$—X—CO—Y—Z as the compound obtained by the reaction described above, and the carboxyl group of carboxymethylcellulose.

$H_2N$—X—CO—Y—Z is preferably introduced into the reaction system at 0.01-0.4 equivalent with respect to the mole equivalents of carboxyl groups of the carboxymethylcellulose starting material. The amount of $H_2N$—X—CO—Y—Z may be in excess considering the reaction efficiency.

The coupling reaction is preferably carried out in a solution containing water, due to the properties of carboxymethylcellulose. In this case, water may be used alone as the reaction solvent or a mixture of water and a compatible organic solvent may be used, and reaction may even be conducted in a two layer system employing an organic solvent that is not compatible with water. As organic solvents that are compatible with water there may be mentioned alcohols such as methanol and ethanol, cyclic ethers such as tetrahydrofuran and dioxane, ethers such as polyethylene oxide compounds, amides such as dimethylformamide and dimethylacetamide, organic bases such as pyridine and piperidine, dialkylsulfones such as dimethyl sulfoxide and ketones such as acetone. Preferably, the reaction is conducted between carboxymethylcellulose and $H_2N$—X—CO—Y—Z in a homogeneous reaction system comprising a mixture of water and a water-compatible organic solvent, and the water-compatible organic solvent is preferably tetrahydrofuran.

The catalyst used for coupling may be any known compound, with carboxyl activating reagents and condensation agents being preferred for use. As carboxyl activating reagents there may be mentioned N-hydroxysuccinimide, p-nitrophenol, N-hydroxybenzotriazole, N-hydroxypiperidine, 2,4,5-trichlorophenol and N,N-dimethylaminopyridine. As condensation agents there may be mentioned 1-ethyl-3-(dimethylaminopropyl)-carbodiimide and its hydrochloride, diisopropylcarbodiimide, dicyclohexylcarbodiimide and N-hydroxy-5-norbornane-2,3-dicarboximide.

Preferred for use among these are N-hydroxybenzotriazole as a carboxy activating reagent and 1-ethyl-3-(dimethylaminopropyl)-carbodiimide hydrochloride as a condensation agent.

The reaction temperature is preferably 0-60° C. The reaction is more preferably conducted at 0-10° C. to inhibit by-products. The reaction environment is preferably weakly acidic and even more preferably pH 6-7.

The hydrogel of the invention is a hydrogel formed by including water in a cellulose derivative of the invention, and specifically it is a hydrogel comprising 0.05-3.0 parts by weight, preferably 0.1-2.0 parts by weight and even more preferably 0.3-1.0 part by weight of a cellulose derivative with the chemical structure represented by formula (1) as a repeating unit, with respect to 100 parts by weight of water.

A preferred hydrogel of the invention is one having sufficient viscoelasticity so that it does not flow off even when the container containing the gel is inclined, and preferably it is easily deformable when touched with a metal spatula such as a flat spoon, is easily coatable onto affected areas, and can be injected with narrow tubular instruments such as syringes. The viscoelasticity of the hydrogel of the invention can be adjusted by varying the amount of cellulose derivative of the invention with respect to the water, thus allowing optimization suited for the purpose of use.

In addition, the hydrogel of the invention is colorless transparent, and therefore contaminants such as dirt can be identified when they become included during the production process, thus providing an advantage for industrial production.

Furthermore, when the hydrogel of the invention is diluted with water, it absorbs the water so that the gel increases in size by the amount of water added. Dilution with water results in eventual solubilization in the water, causing it to lose its gel property and become an aqueous solution.

Other components will be present in the hydrogel of the invention, in addition to water, including the condensation agent used as the catalyst, by-products such as urea generated by the condensation agent undergoing certain chemical reactions, the carboxyl activating reagent, unreacted amines, contaminants that may become included at different stages of the reaction, and ions used to adjust the pH, and these components are preferably limited to a low level such that none of the compounds cause foreign body reactions when the gel is placed in the body.

The preferred complex elastic modulus for the cellulose derivative of the invention is 50-900 $N/m^2$ and more preferably 100-700 $N/m^2$, when measured with a dynamic viscoelasticity measuring apparatus (rheometer) at an angular velocity of 10 rad/sec, under conditions with a polymer concentration of 0.5 wt % in water and a temperature of 37° C. The complex elastic modulus is the constant representing the ratio of the stress and strain of the elastic solid.

The cellulose derivative of the invention and its hydrogel may be used for medical purposes as a biomedical material or the like, for a commodity such as a hair care product or skin humectant, for cosmetic use, and the like. The hydrogel of the invention can also be used as a low invasive medical material since it is injectable through a syringe, and most preferably it is used as a cell carrier for regenerative medicine, a carrier for retention or sustained release of liquid factors such as growth factors, a carrier for retention or sustained release of low molecular compound drugs, or as a biomedical material such as an adhesion barrier or sealant. It may also be suitably used as a cell culture material, microbial culture material or dental implant material. A complex of cells with a cell-cultured molded article can be suitably used for sensing or diagnosis with a cell chip or the like.

The cellulose derivative and its hydrogel according to the invention can be subjected to sterilization treatment by any known sterilization method. Preferred sterilization methods include electron beam irradiation, gas sterilization with ethylene oxide, and high-pressure steam sterilization.

EXAMPLES

Embodiments of the invention will now be explained in greater detail by the following examples, with the understanding that they do not restrict the scope of the invention in any way.

Example 1

Synthesis of $H_2N$—$CH_2$—$CO$—$(O$—$CH_2CH_2)_7$—$O$—$C_{18}H_{35}$

After dissolving 1 millimole of N-butyloxycarbonylglycine (Boc-Gly-OH, Wako Pure Chemical Industries, Ltd.) with respect to 1 millimole of oleyl alcohol polyethyleneglycol ether (H—$(O$—$CH_2CH_2)_7$—$O$—$C_{18}H_{35}$, Wako Pure Chemical Industries, Ltd.) in dichloromethane, a dichloromethane solution containing 1 millimole of dicyclohexylcarbodiimide (Wako Pure Chemical Industries, Ltd.) as a condensation agent was added dropwise at room temperature. The reaction mixture was filtered to remove the dicyclohexylurea by-product and then concentrated and dried to obtain an amino group-protected intermediate (Boc-NH—$CH_2$—$CO$—$(O$—$CH_2CH_2)_7$—$O$—$C_{18}H_{35}$).

Approximately 1-2 ml of trifluoroacetic acid (Wako Pure Chemical Industries, Ltd.) was added to the intermediate, and de-Boc reaction by acid treatment was conducted at room temperature for 2 hours. Progress of the reaction was confirmed by TLC. The reaction mixture was concentrated under reduced pressure, and the excess trifluoroacetic acid was removed to obtain a trifluoroacetic acid salt of an amine compound as the target product. The product was confirmed by $^1$H-NMR.

Example 2

Coupling of carboxymethylcellulose (CMC-Na) and $H_2N$—$CH_2$—$CO$—$(O$—$CH_2CH_2)_7$—$O$—$C_{18}H_{35}$ After dissolving 200 mg of CMC-Na (F600 MC, degree of substitution: 0.69, Nippon Paper Chemicals Co., Ltd.) in 40 ml of water, 40 ml of tetrahydrofuran was further added and mixed therewith to obtain a homogeneous solution. The trifluoroacetate of $H_2N$—$CH_2$—$CO$—$(O$—$CH_2CH_2)_7$—$O$—$C_{18}H_{35}$ synthesized in Example 1 was added and mixed at 0.2 equivalent to 1 equivalent of carboxyl groups in the CMC-Na.

After dissolving EDC (1-ethyl-3-[3-(dimethylamino)propyl]carbodiimide.HCl (Wako Pure Chemical Industries, Ltd.) and HOBt.$H_2O$ (1-hydroxybenzotriazole.monohydrate, Wako Pure Chemical Industries, Ltd.), at 1.1 equivalents each to $H_2N$—$CH_2$—$CO$—$(O$—$CH_2CH_2)_7$—$O$—$C_{18}H_{35}$, in 10 ml of tetrahydrofuran/water=1/1, the solution was added to the reaction system and the mixture was stirred overnight. After stirring, the reaction mixture was concentrated with a rotary evaporator to remove the tetrahydrofuran, the water was evaporated off, and the total amount was concentrated to approximately ⅓, after which the reaction mixture was added to ethanol to form a precipitate. The precipitate was filtered and the resulting precipitate was suspended in ethanol and stirred for 24 hours, and then recovered and vacuum dried to obtain a cellulose derivative. The obtained cellulose derivative was subjected to elemental analysis and the degree of substitution was calculated from the proportion of carbon and nitrogen. As a result, the degree of substitution was 0.16.

Example 3

Preparation of Hydrogel

A 10 mg portion of the cellulose derivative obtained in Example 2 was dissolved in 1990 mg of ion-exchanged water to prepare a hydrogel with a concentration of 0.5 wt %. The obtained hydrogel was colorless transparent, did not flow when the container was inclined, allowed easy insertion of a metal spatula such as a flat spoon, and could be easily pushed through a 25G injection needle.

The complex elastic modulus of the obtained hydrogel was measured to be 177 N/m$^2$. The complex elastic modulus of the hydrogel was measured at 37° C. with an angular velocity of 10 rad/sec, using a Rheometer RFIII (TA Instrument) as the dynamic viscoelasticity measuring apparatus.

Example 4

Intraperitoneal Adhesion Test

Sprague-Dawley (SD) rats (n=10) by Charles River Laboratories, Japan Inc. were used to prepare an intraperitoneal adhesion model according to the method of Buckenmaier C C 3rd et al. [Buckenmaier C C 3rd, Pusateri A E, Harris R A, Hetz S P: Am Surg. 65(3):274-82, 1999]. Specifically, the rats were fixed in the supine position under anesthesia by intraperitoneal administration of pentobarbital sodium, and after shaving the abdominal regions, they were treated with ethanol for disinfection. After then disinfecting the surgical region with Isojin antiseptic solution, a 3-4 cm incision was made along the median line of the abdominal region to expose the cecum. A prescribed area (1-2 cm$^2$) of the exposed cecum was abraded to petechia using sterile gauze. The cecum was restored and a defect (8 mm×16 mm) was made in the corresponding abdominal wall. Next, the defect site of the abdominal wall was coated with a hydrogel (1 ml) prepared by dissolving 10 mg of the cellulose derivative obtained in Example 2 in 990 mg of distilled water for injection, to a concentration of 1.0 wt %. A continuous suture was formed in the muscle layer of the incision site, and then 4-5 needle sutures were made in the skin. The wound was then disinfected with Isojin antiseptic solution, and the rats were returned to their cages. At 4 weeks after preparation of the model, the animals were laparotomized under pentobarbital sodium anesthesia and the degree of intraperitoneal adhesion was observed with the naked eye and scored based on the following scale.

(Scoring)
Score 0: No adhesion observed.
Score 1: Weak adhesion that could be released with a weak traction.
Score 2: Medium adhesion that could withstand a weak traction.
Score 3: Very strong adhesion.

When an adhesion was observed, a gem clip was sewn onto the cecum with suture thread and pulled with a Metric Gauge (EW-93953-05, Cole-Parmer), measuring the maximum strength at which the cecum was separated from the abdominal wall (unit: gf, 1 gf≈0.00981N), and this value was used as the adhesion strength. A value of 0 gf was assigned for no adhesion.

As a result, the adhesion score and strength were 0.8±1.3 and 122.6±203.5 gf, respectively (mean±SD).

Comparative Example 1

As a control, the same procedure was carried out as in Example 4 without coating the hydrogel, and the adhesion and strength were evaluated. As a result, the adhesion score and strength were 1.4±1.5 and 331.2±364.9 gf, respectively (mean±SD).

After 4 weeks, strong adhesion was produced in Comparative Example 1, while the degree of adhesion and strength were notably reduced in Example 4. This demonstrated that the hydrogel obtained in Example 3 had an effect of notably inhibiting adhesion in vivo, thus allowing post-surgical adhesion to be effectively prevented.

INDUSTRIAL APPLICABILITY

The cellulose derivative of the invention forms a hydrogel with high viscoelasticity and can remain at prescribed sites in the body, and it is therefore useful for protecting wounds and forming physical isolation barriers between organs.

In addition, including a drug into the hydrogel of the invention can produce a local drug delivery system.

Moreover, the property of decomposing or being absorbed upon injection into the body renders the hydrogel of the invention suitable for use as an injection gel material or a scaffolding material for regenerative medicine.

Other uses include use in commodities including hair care products and skin humectants or in cosmetics. It may also be used as a cell culture material, microbial culture material or dental implant material. A complex of cells with a cell-cultured molded article can be used for sensing or diagnosis with a cell chip or the like.

What is claimed is:

1. A cellulose derivative comprising the chemical structure represented by the following formula (1) as a repeating unit:

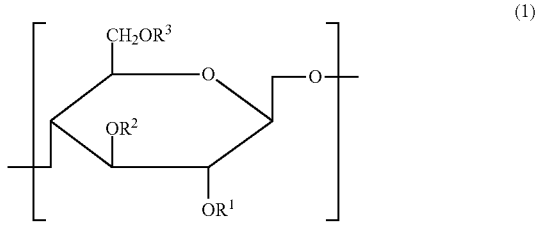

(1)

wherein in formula (1), $R^1$, $R^2$ and $R^3$ are each independently selected from the group consisting of the following formulas (a), (b) and (c):

—H (a)

—$CH_2$—COOM (b)

—$CH_2$—CO—NH—X—CO—Y—Z (c)

where in formula (b), M is hydrogen, an alkali metal or an alkaline earth metal, and in formula (c), X is a C1-10 divalent hydrocarbon group, Y is a divalent group derived from polyalkylene oxide with oxygen atoms at both ends, and Z is a C1-24 hydrocarbon group or —CO—$R^4$ (where $R^4$ is a C1-23 hydrocarbon group);

wherein at least one of $R^1$, $R^2$ and $R^3$ comprises formula (c);

wherein substituent (c) is present in a degree of substitution of 0.001 to 0.50; and wherein the cellulose derivative has a weight-average molecular weight of from $1 \times 10^3$ to $5 \times 10^6$.

2. The cellulose derivative according to claim 1, wherein the ratio of the degree of substitution of substituent (c) to the degree of substitution of substituent (b) is 0.01-0.4.

3. The cellulose derivative according to claim 1, wherein the number of alkylene oxide repeating units in the polyalkylene oxide in Y is 2-100.

4. A hydrogel comprising 0.1-2.0 parts by weight of a cellulose derivative according to claim 1 with respect to 100 parts by weight of water.

5. A medical material comprising a cellulose derivative according to claim 1.

6. An adhesion barrier comprising a cellulose derivative according to claim 1.

7. The cellulose derivative according to claim 2, wherein the number of alkylene oxide repeating units in the polyalkylene oxide in Y is 2-100.

8. A hydrogel comprising 0.1-2.0 parts by weight of a cellulose derivative according to claim 2 with respect to 100 parts by weight of water.

9. A hydrogel comprising 0.1-2.0 parts by weight of a cellulose derivative according to claim 3 with respect to 100 parts by weight of water.

10. A hydrogel comprising 0.1-2.0 parts by weight of a cellulose derivative according to claim 7 with respect to 100 parts by weight of water.

11. A medical material comprising a cellulose derivative according to claim 2.

12. A medical material comprising a cellulose derivative according to claim 3.

13. A medical material comprising a cellulose derivative according to claim 7.

14. An adhesion barrier comprising a cellulose derivative according to claim 2.

15. An adhesion barrier comprising a cellulose derivative according to claim 3.

16. An adhesion barrier comprising a cellulose derivative according to claim 7.

* * * * *